United States Patent
Kuehne et al.

(10) Patent No.: US 11,958,647 B2
(45) Date of Patent: Apr. 16, 2024

(54) METHODS FOR MANUFACTURING NON-GLASS PREFILLED SYRINGES

(71) Applicant: Medline Industries, LP, Northfield, IL (US)

(72) Inventors: Kelly Kuehne, Williamston, MI (US); Curt Carpenter, Webberville, MI (US); Jessica Leginski, Houston, TX (US)

(73) Assignee: Medline Industries, LP, Northfield, IL (US)

( * ) Notice: Subject to any disclaimer, the term of this patent is extended or adjusted under 35 U.S.C. 154(b) by 0 days.

(21) Appl. No.: 17/855,912

(22) Filed: Jul. 1, 2022

(65) Prior Publication Data

US 2022/0332453 A1    Oct. 20, 2022

Related U.S. Application Data

(63) Continuation of application No. 15/169,962, filed on Jun. 1, 2016, now abandoned.

(51) Int. Cl.
   *B65B 55/10*   (2006.01)
   *A61L 2/10*    (2006.01)
   (Continued)

(52) U.S. Cl.
   CPC .......... *B65B 55/10* (2013.01); *A61L 2/10* (2013.01); *A61L 2/206* (2013.01); *A61M 5/001* (2013.01);
   (Continued)

(58) Field of Classification Search
   CPC ....... B65B 3/003; B65B 55/02; B65B 55/027; B65B 55/10; A61M 5/001; A61M 5/002;
   (Continued)

(56) References Cited

U.S. PATENT DOCUMENTS 2,075,845 A * 4/1937 Gross et al. .......... A61L 2/206
                                              514/475
5,039,485 A * 8/1991 Conviser et al. ....... A61L 2/206
                                              422/28
(Continued)

FOREIGN PATENT DOCUMENTS

JP    2002505921    2/2002
JP    2004530465    10/2004
(Continued)

OTHER PUBLICATIONS

"EtO Sterilization: Principles of Process Design," Medical Device & Diagnostic Industry Magazine, Dec. 1, 1998, 11 pages. (Year: 1998).*

(Continued)

*Primary Examiner* — Stephen F. Gerrity
(74) *Attorney, Agent, or Firm* — Fitch, Even, Tabin & Flannery LLP

(57) ABSTRACT

A method of sterilizing a prefilled syringe comprises assembling a syringe assembly and performing at least one ethylene oxide (EtO) sterilization procedure cycle. The assembling step includes inserting a tip cap at a first end of a plunger, filling a non-glass barrel with sterilization sensitive material at a second end of the barrel, and inserting the plunger into the barrel at a second end to seal the sterilization sensitive material within the barrel. The EtO sterilization procedure cycle comprises undergoing a preprocessing stage, a wash and conditioning stage, an EtO sterilization stage and a wash and post exposure stage. Upon completing the EtO sterilization procedure cycle, a resultant pH of the sterilization-sensitive material does not exceed an acceptable pH range as defined by the United States Pharmacopeia. The disclosure also discusses inserting an assembled pre- (Continued)

filled syringe into a procedure tray prior to performing the EtO sterilization procedure cycle.

28 Claims, 6 Drawing Sheets

(51) Int. Cl.
    *A61L 2/20*     (2006.01)
    *A61M 5/00*     (2006.01)
    *A61M 5/31*     (2006.01)
    *A61M 5/315*     (2006.01)
    *B65B 3/00*     (2006.01)
    *B65B 55/02*     (2006.01)

(52) U.S. Cl.
    CPC .......... *A61M 5/002* (2013.01); *A61M 5/3129* (2013.01); *A61M 5/31501* (2013.01); *B65B 3/003* (2013.01); *B65B 55/027* (2013.01)

(58) Field of Classification Search
    CPC ... A61L 2/206; A61L 2202/14; A61L 2202/23
    USPC ................. 53/425, 167; 422/28–37
    See application file for complete search history.

(56) References Cited

U.S. PATENT DOCUMENTS

| | | | | |
|---|---|---|---|---|
| 6,231,810 | B1* | 5/2001 | Tunc | A61L 2/206<br>422/30 |
| 6,488,890 | B1 | 12/2002 | Kirckof | |
| 2002/0119074 | A1* | 8/2002 | McGowan, Jr. | A61L 2/206<br>422/26 |
| 2002/0172615 | A1* | 11/2002 | Woodworth | B65B 55/08<br>422/22 |
| 2004/0004019 | A1* | 1/2004 | Busch | A61M 5/002<br>206/370 |
| 2005/0089442 | A1* | 4/2005 | Young et al. | A61L 2/206<br>422/4 |
| 2010/0313962 | A1* | 12/2010 | Bondar et al. | A61L 2/206<br>422/105 |
| 2013/0280346 | A1* | 10/2013 | Powers et al. | A61L 2/206<br>424/663 |
| 2013/0296779 | A1* | 11/2013 | Kuehne | B65B 3/003<br>604/93.01 |
| 2016/0310622 | A1* | 10/2016 | Goetz et al. | A61L 2/206 |

FOREIGN PATENT DOCUMENTS

| | | | | |
|---|---|---|---|---|
| JP | 2006314554 A | * | 11/2006 | ............ A61M 5/002 |
| JP | 2015515480 | | 5/2015 | |
| JP | 2015519125 | | 7/2015 | |
| JP | 2015521530 | | 7/2015 | |
| WO | WO-2014155562 A1 | * | 10/2014 | ............... A61L 2/07 |
| WO | WO-2015094879 A1 | * | 6/2015 | ............. A61L 2/206 |

OTHER PUBLICATIONS

Japan Medical Devices Society, Guideline for Sterility Assurance in Healthcare Settings 2015, dated May 25, 2015, 37 pages.

\* cited by examiner

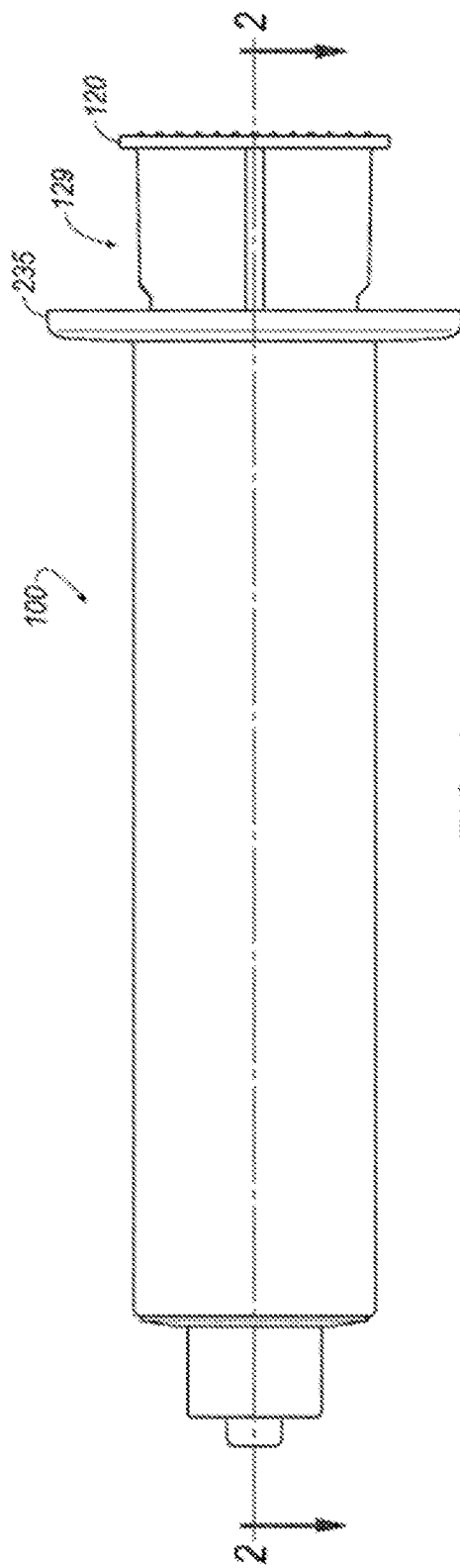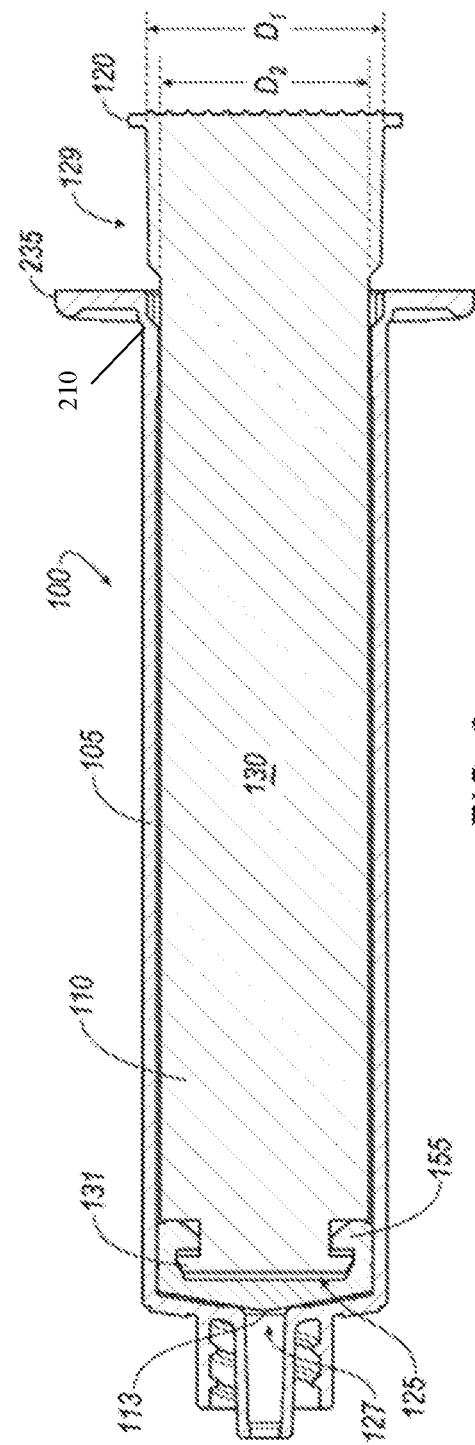
FIG. 1
FIG. 2

METHODS FOR MANUFACTURING NON-GLASS PREFILLED SYRINGES

RELATED APPLICATIONS

This application is a continuation of U.S. application Ser. No. 15/169,962, filed Jun. 1, 2016, the content of which is incorporated herein by its entirety.

FIELD OF TECHNOLOGY

The present disclosure relates to ethylene oxide ("EtO") gas sterilization methods for sterilizing non-glass containers that are at least partially prefilled with material that is sensitive to sterilization techniques including, but not limited to, containers prefilled with saline (0.9% NaCl saline, heparinized saline, or lidocaine), without causing EtO ingress gas ingress into the prefilled container.

BACKGROUND

Syringes have been in use for many years. However, syringes were typically made of glass. Gradually with the discovery of plastic materials, some syringes began to be offered in plastic. In recent history, a number of plastic syringe manufacturers, medical device manufacturers and/or drug companies began offering prefilled plastic containers, including vials and syringes, with fluid material, such as saline, heparinized saline or lidocaine. However, as discovered by the syringe manufacturers these materials are sensitive to certain sterilization techniques. For example, IV flush solutions, drugs, vaccines or other fluid materials that contain saline solution may experience a change in their respective composition or properties, such as an undesirable pH shift of the saline solution, when saline contents in the plastic container is exposed to ethylene oxide ("EtO") gas sterilization. Further, the potency of heparinized saline and/or lidocaine may be adversely affected, and EtO gas residual, and/or residual toxic byproducts may be created when the solution is exposed to certain sterilization techniques after filling is accomplished.

Pre-filled syringes manufactured from plastic materials, such as polypropylene have been found to lead to various complications. For example, the United States Pharmacopeia ("USP") guidelines require that normal saline solution (i.e., 0.9% NaCl) in prefilled syringes may only possess a pH between 4.5 and 7.0 to be suitable for human use. It has been determined that one complication that frequently occurs with known prefilled containers is an undesired shift in pH following ethylene oxide gas (EtO) sterilization. PH has been identified as an indicator of EO ingress, such that if the pH of the fluid within the syringe had shifted (usually +, or higher) outside of accepted USP standards limits, one or more of the other parameters indicative of suitable for human use (as discussed in further detail below), were also exceeded.

Commercially available prior a prefilled saline and heparinized saline syringes and a vial for IV flushes were obtained for a testing regimen performed and designed for assess state of the art for prefilled plastic containers, such as syringes and vials. Tests were performed on control samples that had not be subjected to EtO sterilization, as well as on groups of EtO sterilized samples. Upon completion of the EtO sterilization process, the pH level of all of the samples were tested. The tests revealed that the commercially available samples demonstrated an undesirable pH shift, such that the pH of the saline exceeds the range permitted by the USP after being subjected to EtO sterilization. Each of the test groups subjected 10 samples from different prior art manufacturers. The average amount of pH shift from the control samples indicated unacceptable pH shifts, which resulted in the pH of the saline falling outside of the mandated pH range of 4.5 to 7.0:

| Test Syringe | Avg. fluid pH shift (from controls) |
|---|---|
| Prior Art Group 1 | +3.87 |
| Prior Art Group 2 | +3.97 |
| Prior Art Group 3 | +4.49 |
| Prior Art Group 4 | +5.27 |
| Prior Art Group 5 | +4.10 |
| Prior Art Group 6 | +4.26 |
| Prior Art Group 7 | +4.45 |
| Prior Art Group 8 | +4.96 |
| Prior Art Group 9 | +4.74 |
| Prior Art Group 10 | +4.99 |
| Prior Art Group 11 | +4.51 |

This undesirable shift is determinative of EO ingress into the syringe/container, during the EtO sterilization process.

However, it is desirable to pack-age prefilled syringes containing sterilization-sensitive fluid material with other medical procedural tools and/or equipment requiring sterilization in a medical procedural tray, kit, pouch or other packaging. For example, collectively packaged convenience kits such as surgical or procedural kits may include prefilled syringes, as well as surgical instruments, gloves, dressings, aseptic wipes, etc.—all requiring EtO sterilization, which are necessary to perform a given medical procedure. In such instances where prefilled syringes that include sterilization-sensitive fluid material are incorporated in such convenience kits, one known way to avoid the problems created by the use of plastic pre-filled syringes is to utilize glass containers and glass syringes due to the barrier properties of glass, as glass effectively prevents the above identified undesirable effects of EtO ingress to the fluid material.

However, while glass containers have proven to be a suitable barrier for enabling EtO sterilization, glass containers have certain limitations that leave this choice of material undesirable. As one example, glass containers are fragile. As a result, there is a danger of the sterilization-sensitive material attacking the surface of the glass material, or that the glass may sliver and contaminate the material therein. As another example, microcracks in the glass may permit penetration of EO and/or the glass container may explode during deep sterilization cycle vacuums. Other issues caused by the fragility of the glass include breakage of the syringe if the syringe is dropped. While broken glass may be cleaned up, if the syringe is dropped during a procedure in the operating room, such clean-up might require shutting the operating room down (at significant financial cost to the facility) to recreate a sterile field, as well as delaying patient care. Further, glass is much more costly to manufacture as compared to plastic, and has inherent limitations relating to geometry, size and intricacy of the container. Transporting glass, including with sterilization sensitive material therein and transporting used glass syringes after use, is much more expensive than plastic due to the weight of the material, in addition to the extra care that must be taken to avoid breakage. Finally, glass syringes have additional issues, in that an integrated medical industry standard luer tip cannot be created for a glass syringe. Instead, an adapter must also be provided to incorporate a luer fitting, thereby increasing costs.

One method of addressing the known EtO sterilization limits inherent to plastic containers is to sterilize an empty plastic syringe and then fill the plastic syringe with sterile fluid (introducing the sterile fluid in a clean room or aseptic environment). The filled syringe is then packaged in a non-sterile pouch. This method provides a "sterile fluid pathway" but the syringe exterior itself is not sterile. More specifically, the outside of the syringe is not sterile. As a result, the syringe must be separately packaged from the rest of the procedure kit, thereby creating two different SKU numbers, which may complicate inventory tracking and create end clinical user inconvenience and inefficiency. In one example, the non-sterile, prefilled container is attached to the exterior of a sterile kit post-sterilization of the kit, sometimes referred to as a "sidecar" package, thereby creating a secondary non-sterile kit comprised of a non-sterile prefilled container and a sterile kit. While this combination kit may reduce inventory tracking, the added step of separately packaging plastic containers and attaching them to sterilized kits makes manufacturing and assembly more time consuming and expensive. In addition, there is a danger that the sidecar package may become detached and lost in the medical facility, which then may result in unnecessary waste, as well as delaying the procedure while new material is located.

In addition, for a fully wrapped "liftout" surgical kit of components inside of a sterile tray, the syringe components are not inside the wrapped assemblies. Instead, these syringe components must be separately unpackaged and loaded onto the surgical wrap/drape, after the wrap/drape is opened within the sterile field.

Another known method to address known EtO sterilization limits inherent to plastic containers is to fill an empty plastic syringe with fluid material, which may be introduced as sterile fluid in a clean room or aseptic environment, as discussed above. The filled plastic syringe may then be autoclaved, which will ensure that a sterile fluid and fluid pathway results. However, the outside of the syringe still remains non-sterile and may be packaged as described above.

Moreover, maintaining sterile technique during a clinical procedure becomes more challenging when a separately packaged, non-sterile component must be handled. This may affect the sequence of actions required to complete a given procedure, or, in some cases, the number of physicians needed to complete a procedure. For example, during a procedure, a nurse must open the non-sterile package outside of the sterile field and once the Doctor touches the syringe, the procedure must be adjusted to maintain the sterile technique.

As another solution, a filled "sterile fluid path" syringe may be steam sterilized. Upon steam sterilization, the syringe is then placed in an EtO gas impermeable foil package, which is then introduced into a procedural kit, with the kit and foil package being EtO sterilized together. The foil package prevents the EtO gas inside the procedural kit from getting through the foil package, and thus prevents EtO gas from interacting with the fluid material within the syringe. However, this process is also time consuming and expensive, as it requires two separate sterilization processes. Moreover, in use, it then requires a clinician to open multiple packages during a procedure and move it to the appropriate location in the sterile field, as well as requiring proper disposal of the packaging components without compromising the integrity of the sterile field.

In an another solution, the prefilled syringes containing sterile solution (though the exterior of the syringe was not sterile), is packaged in a sleeve that may be attached to lidding or a pouch of the kit. Once packaged, the sleeve may be autoclaved so that the packaged syringe is sterile field ready. However, this arrangement then requires an extra person to open the packaging to drop the syringe within the sterile field. This arrangement does not permit having the syringe in an EtO sterilizable procedure kit.

It is desired to address one or more such limitations experienced with known glass containers, plastic containers, packaged kits, and/or methods disclosed herein.

BRIEF DESCRIPTION OF THE DRAWINGS

FIG. 1 illustrates a side view of an exemplary syringe assembly;

FIG. 2 illustrates a cross-sectional view of the syringe assembly of FIG. 1, taken along lines 2-2;

DETAILED DESCRIPTION

Figure 3A:
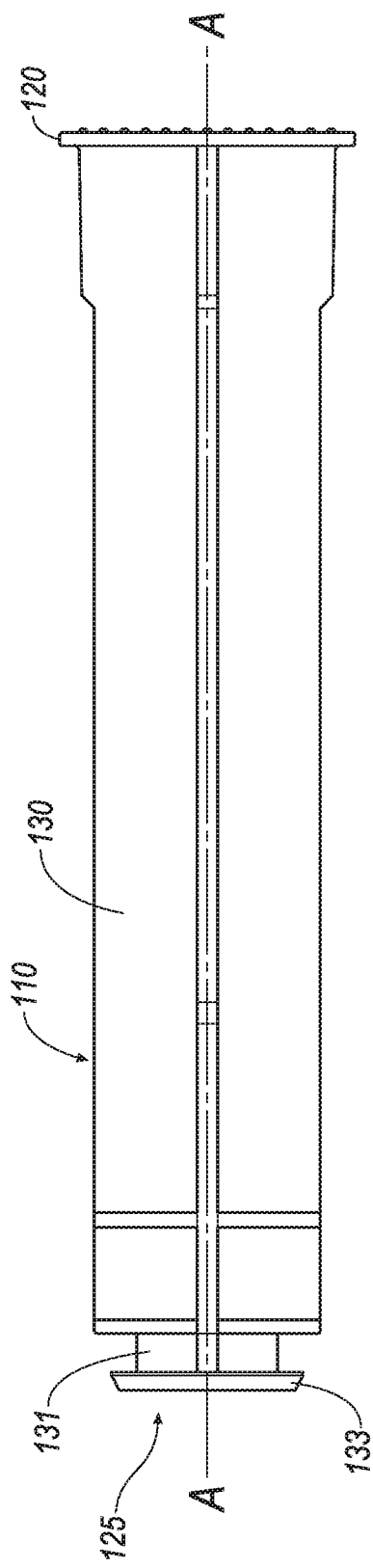
FIG. 3A illustrates side view of an exemplary plunger assembly for use with the syringe assembly of FIG. 1.

Referring now to the drawings, illustrative examples are shown in detail. Although the drawings represent certain examples, the drawings are not necessarily to scale and certain features may be exaggerated to better illustrate and explain an innovative aspect of an example. Further, the examples described herein are not intended to be exhaustive or otherwise limiting to the precise form and configuration shown in the drawings and disclosed herein.

A prefilled container system may include a syringe assembly having a barrel, plunger and tip cap. A chamber may be formed within the barrel between the plunger and tip cap and may be configured to hold sterilization sensitive materials such as saline or heparinized saline. The syringe assembly may be formed of various materials and/or solutions that permit the syringe assembly to be packaged with a surgical kit containing other items necessary to perform a medical procedure and sterilized together. For example, as determined by medical professionals such as nurses, surgeons and other operating room staff, such kits may be tailored to particular procedures and may include items such as instruments, drugs, antiseptics, dressings that are appropriate and needed for the particular procedure. For convenience, as well as to reduce inventory burden (such as tracking) it is preferred that individual items not be separately packaged.

As another key advantage, providing a sterile convenience kit permits operating room staff to maintain established sterile techniques in performing surgical operations, such that there is no need to separately remove the syringe from separate packaging and locate the syringe in the sterile field.

For health and sanitary purposes, it may be desired and necessary that all items within the kit be sterilized and ready for use by the medical professionals. During manufacturing, the items within the kit may be sterilized to eliminate live bacteria or other microorganisms present on the inside or outside of the kit, and inside and outside of any component item within the sterile kit. Known sterilization methods may include EtO sterilization, autoclaving, or other methods such as irradiation. In one embodiment, terminal sterilization is used as the sole sterilization step in the assembling and manufacturing of the packaged kits. However, as explained above, the EtO gases used during terminal sterilization may alter the composition of sterilization sensitive material within a syringe.

Figure 6A:
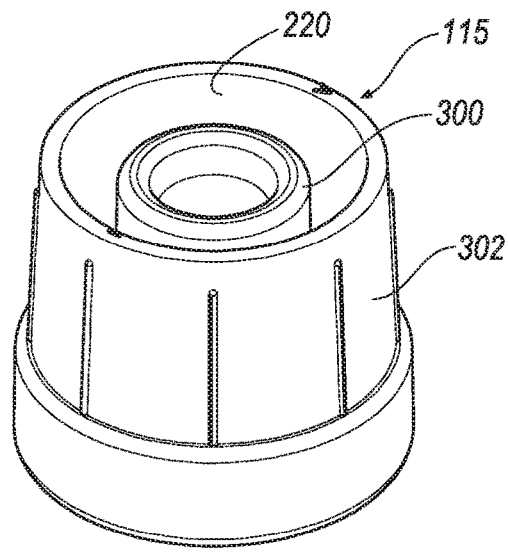
FIG. 6A illustrates a perspective view of a tip cap assembly.
Figure 6B:
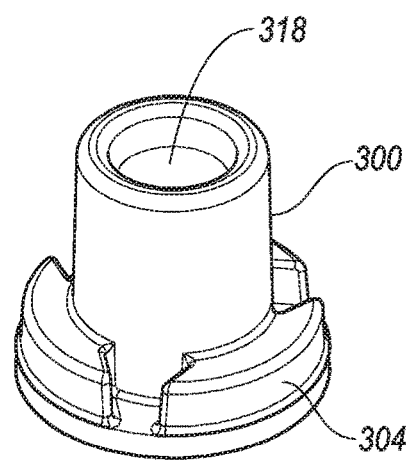
FIG. 6B illustrates a perspective view of a tip cap insert of the tip cap assembly of FIG. 6A.

Accordingly, a syringe assembly 100, as shown in FIG. 1, may include a barrel 105, a plunger 110 and a tip cap 115 (shown in FIG. 6A). The interior of the barrel 105 may cooperate with a distal end 113 of the plunger 110 and the tip cap 115, when assembled to the barrel 105, to define a chamber 230 (best seen in FIG. 4A). Any number of solutions (i.e., material) may be included in the chamber 230. Examples of preferred solutions include, but are not limited to, sodium chloride (such as 0.9% NaCl saline), heparinized saline (various amounts of heparin content), lidocaine or other liquid medication for infusion, or catheter lumen line flushing. The solution may also include active ingredients such as vaccines, drugs, probiotics, diagnostic compositions, etc. Typically, the chamber contents are a liquid solution that is sterile; either by an aseptic filling process or post filling terminal sterilization that provides a sterile fluid path. These solutions, when included in a procedural kit, may be adversely affected by the terminal kit sterilization process, such as EtO sterilization as explained above. However, the kit sterilization is necessary to ensure all the contents of the finished procedural kit are sterile.

The contents of plastic containers, as described above, may be compromised during the kit sterilization process and, therefore, the solution contained therein may be affected and considered "sterilization sensitive." For example, EtO sterilization may include subjecting the filled syringe assembly 100 to EtO gas. The use of EtO gas is effective and an accepted procedure to kill any microorganisms and ensure that the assembly 100 is sterilized prior to use. However, as recognized by Federal Drug Administration (FDA), the EtO gases may alter the composition of the sterilization sensitive solution. Thus, as set out in the notice of rulemaking published by the FDA in the Federal Drug Administration, 43 Fed. Reg. 122 at 27474-27483 (proposed Jun. 23, 1978) (to be codified at 21 C.F.R. § 221 and § 821) ("Ethylene Oxide, Ethylene Chlorohydrin, and Ethylene Glycol—Proposed Maximum Residue Limits and Maximum Levels of Exposure") the contents of which are incorporated by reference in its entirety, the amount of residual Ethylene Oxide (EO) gas, Ethylene Chlorohydrin (ECH) and Ethylene Glycol (EG) toxic by-products present in an injectable drug must be tightly controlled. For injectable drugs, the FDA guidance document suggests that the residual EO and ECH shall not exceed 10 ppm and the residual EG shall not exceed 20 ppm. In addition, the FDA guidelines also set maximum daily exposure level requirements. More specifically, for EO, the maximum daily exposure level is 30 µg/kg/day up to 30 days. For ECH, the maximum daily exposure level is 15 µg/kg/day up to 30 days. And for EG, the maximum daily exposure level is 2.5 mg/kg/day up to 30 days. While the above proposed limits for residual EO, ECH and EG were never published as a final rile, these limits have been used and accepted by both industry and government as a de facto regulation for more almost 40 years.

With specific reference to sodium chloride injections, the U.S. Pharmacopeia (USP)—National Formulary has provided a test standard for an acceptable pH in such solutions. More specifically, the pH should be in the range of 4.5-7.0 (test no. 791). The inventors of the present application have determined that a pH shift outside of this range is an indicator for undesirable EO ingress in a chamber 230 of a syringe. For example, as set forth in the background, testing of samples prior to undergoing a EtO sterilization process, yielded a baseline pH, well within the USP range of 4.5-7.0. However, once those prior art samples were subjected to prior art EtO sterilization techniques, the pH shifted outside the UPS range, thereby revealing that the solution within the syringes had been altered.

The USP also sets forth an acceptable pH range for other injectable solutions that are contemplated by this disclosure, such as lidocaine hydrochloride and epinephrine injections (pH in the range of 3.3-5.5), lidocaine hydrochloride injections (pH in the range of 5.0-7.0), and heparin lock flush solutions (pH in the range of 5.0-7.0).

While the above USP standard is directed to the material within the chamber 230, the syringe assembly 100 itself also is subject to maximum residue limits. More specifically, the syringe is classified as a medical device and is subject to ANSI/AAMI/ISO 10993-7:2012 "Biological Evaluation of Medical Devices—Part 7: ETO Sterilization Residuals. For those medical devices subject to EtO Sterilization techniques, the residual EO gas in the device must be less than or equal to 4 mg per device, while the residual ECH toxic by product must be less than or equal to 9 mg/device. Currently there is no standard for residual EG toxic byproduct.

To provide a syringe assembly 100 that conforms to the above FDA requirements, as well as the relevant ISO standards, as explained in further detail below, the syringe assembly 100 provides that the chamber 230 is capable of creating an effective barrier between sterilization gases and the solution so that the solution remains substantially unchanged within the chamber 230 during and after sterilization. For example, in one exemplary arrangement, by the term "substantially unchanged," the pH of the solution stays with the range of about 4.5-7.0. The inventors of the present application have determined that small shifts of the pH of the solution that results in a post-sterilization pH still within the range of about 4.5-7.0 is indicative that the sterilization technique has not caused ingress of EtO gas into the solution via any known entry points and pathways (through the barrel, any rubber interfaces, any silicone lubricant, interface areas (tip cap)) of the assembly 100 and has therefore not adversely affected the solution contained within the chamber 230. Thus, the solution remains within acceptable specifications for the manufacture, sale, and use of the device. The inventors have discovered these unexpected results after numerous experiments with different plastic material for assembly 100, in combination with variations of sterilization cycle parameters, which will be discussed below in further detail. As another example, if the solution remains substantially unchanged after exposure to sterilization, then the device and solution still meets the regulatory requirements for the manufacture, sale, and use of that drug, i.e., is also has residual EO gas and ECH toxic byproduct that does not exceed 10 ppm and the residual EG toxic byproduct that does not exceed 20 ppm.

In an exemplary configuration of the syringe assembly 100, the plunger 110, as shown in FIGS. 1-3, may include a plunger body 130 extending along an axis A and having a base 120 at one end and a stopper mount 125 disposed at the opposite end of the plunger body 130. The stopper mount 125 is configured to receive a plunger stopper 127. The plunger body 130 may be made of a light-weight material. As explained in further detail below, because the plunger body 103 does not come into contact with the solution disposed in barrel 230, there are several options for the material for the plunger body 103. In one exemplary arrangement, the plunger body 103 may be fabricated from polypropylene, which is low in cost, as well as being lightweight.

In one exemplary configuration, the stopper mount 125 comprises an extension element 131 that extends distally from the plunger body 130. Extension element 131 has a diameter that is slightly smaller than the diameter of the plunger body 130. A mounting flange 133 is secured to the distal end of the extension element 131. This configuration provides a mounting channel between the mounting flange 133 and the distal end of the plunger body 130. The mounting channel is configured to receive an annular retainer 155 of the stopper 127, as shown in FIG. 2, for example.

Figure 3B:
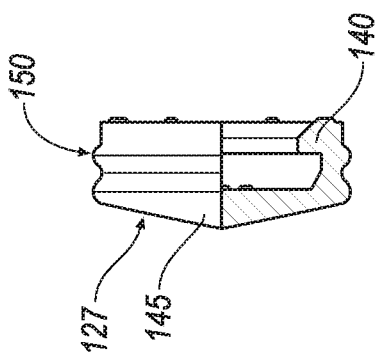
FIG. 3B illustrates a side view of an exemplary plunger tip for use with the plunger of FIG. 3A.

As shown best in FIG. 3B, the stopper 127 may include a cylindrical portion 140 and an end portion 145, which may have a conical shape. The cylindrical portion 140 may also include at least one wiper 150 extending radially around the cylindrical portion 140. As discussed above, in one exemplary arrangement, the stopper 125 may be connected to the extension element 131 of the plunger body 130 via a retainer 155. In one exemplary arrangement, the attachment mechanism 155, as shown in FIG. 3B, includes an annular retainer 155 that extends inwardly from an outside surface and is configured to be frictionally engaged within the mounting channel of the extension element 131. However, it is understood that other connection arrangements are contemplated. For example, a suitable attachment member may include a male and female connection mechanism, whereby the stopper 125 may define an opening (not shown) configured to receive a post (not shown) extending outwardly along the axis A of the plunger body 130 so as to frictionally engage the stopper 125. Further, a suitable attachment mechanism 155 may also include an adhesive such as glue may be used. Additionally or alternatively other mechanisms may be used such as a screw mechanism, hook and eye mechanism, etc.

The stopper 125 may have relatively a stiff elastic modulus and be formed from one or more materials, including high barrier thermoplastic elastomers. Exemplary elastomers may include, but are not limited to, butyl rubber or bromobutyl rubber. The stopper 125 may also be coated for increased barrier properties to EO ingress, such as, for example, with silicone lubricant of appropriately selected centistokes viscosity. In addition, a suitable coating may provide smooth operating/slide friction, with no unintended plunger movement during the many environmental pressure changes imparted on the assembly 100 during the various EtO sterilization cycle parameters.

The base 120 of the plunger 110 may be formed so as to be co-extensive with the plunger body 130 and thus include similar materials in one exemplary arrangement, the plunger body 130 is configured to angle inwardly from a first diameter $D_1$ to a second $D_2$ to a second diameter at the proximal end 129 of the plunger body 130. This configuration serves to limit movement of the plunger body 130 within the barrel 105. The base 120 is sized to be greater than the first diameter $D_1$ so as to provide a land area for activating movement of the plunger 130 within the barrel 105 during use. As explained above, during sterilization, the base 120, and at least a portion of the plunger body 130 may be exposed to EtO gases. However, the plunger body 130 and base 120 does not come into contact with the sterilization sensitive material within the chamber 230. Thus, at least one of the base 120 and plunger body 130 may be formed of less expensive plastics such as polypropylene or polycarbonate.

Figure 4A:
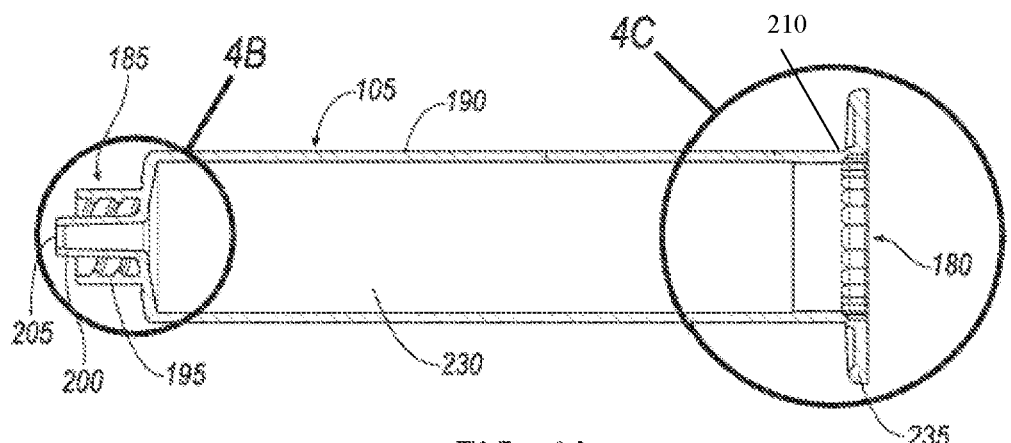
FIG. 4A illustrates a side view of a barrel of the exemplary syringe assembly of FIG. 1.
Figure 4B:
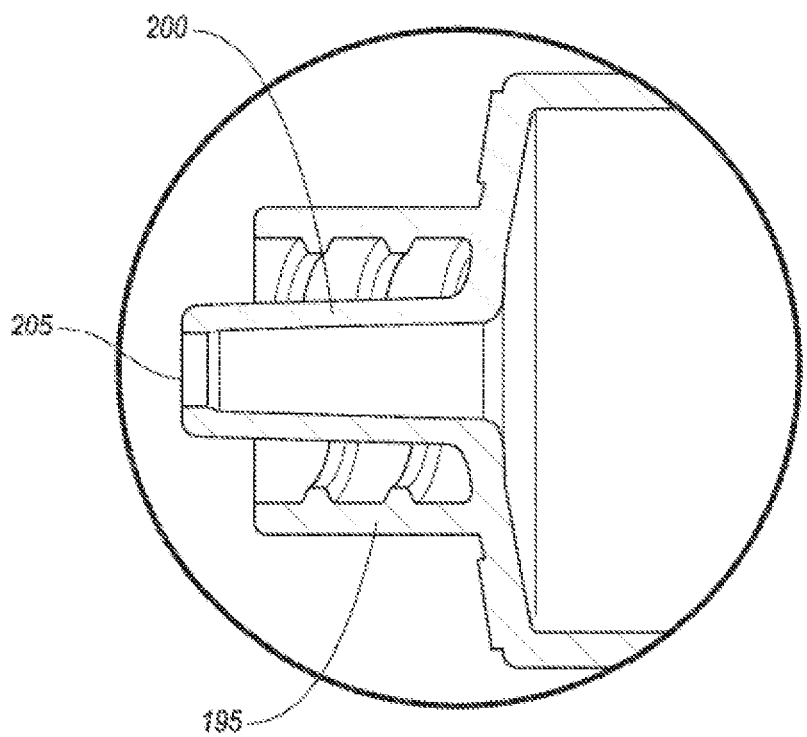
FIG. 4B illustrates an enlarged view of an exemplary barrel neck of the barrel of FIG. 4A.

The barrel 105, as shown in FIGS. 2 and 4A, includes a first end 180, a second end 185 and a barrel body 190 extending therebetween. The barrel body 190 may form a cylindrical shape extending along the axis A. The first end 180 may be an open end configured to receive the plunger 110 so as to provide a fluid tight seal. The second end 185 may include a barrel neck 195. In one exemplary arrangement, the neck 195 may include a male luer 200 defining an opening 205.

Figure 4C:
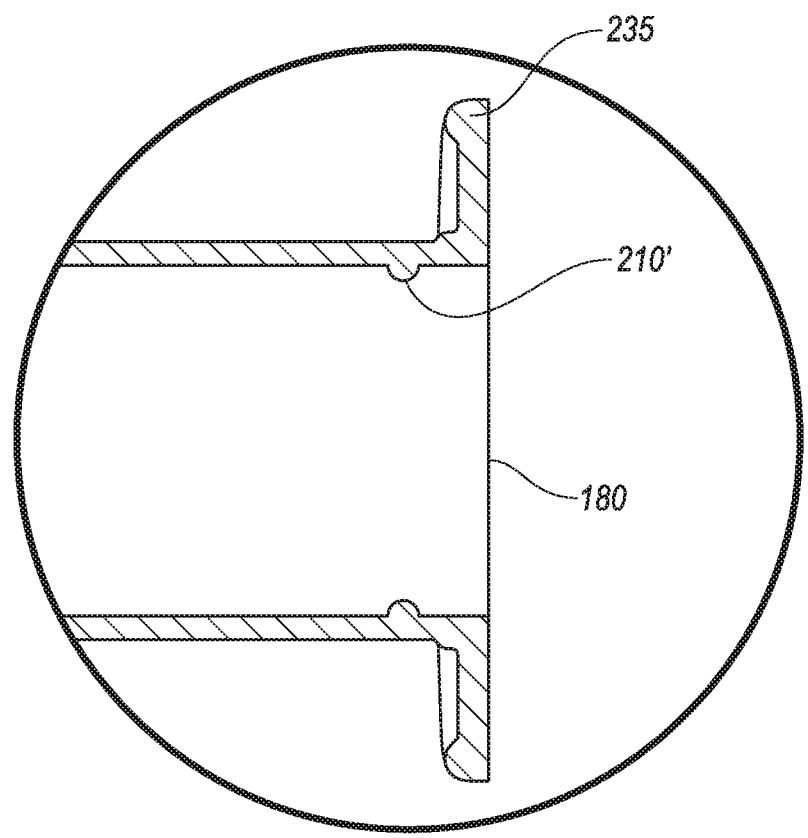
FIG. 4 C illustrates an enlarged view of an alternative arrangement of a proximal end of the barrel of FIG. 4A.

The barrel 105 may also include a mechanical engagement system, or barrel flange 210, extending radially inwardly of an inner surface of the barrel 105 adjacent the first end 180. More specifically, as shown in FIG. 4A, the inner surface of the barrel 105 adjacent the first end 180 of the barrel 105 may have a cross-sectional thickness that is greater to as to extend toward a central axis extending through the barrel 105. With this arrangement, a barrel flange 210 is formed. During EtO sterilization, a positive pressure differential may be created within the barrel 105 (relative to the pressure outside the barrel, which may be negative). This differential may apply a force against the plunger 110, attempting to force the plunger 110 out of the barrel 105, and leaking fluid from the barrel 105. The barrel flange 210 may be configured to engage the outer periphery of a plunger flange and/or the wipers 150 of the stopper 125 to prevent the plunger 110 from complete expulsion from the barrel 105. Other exemplary mechanical engagements may include one or more protrusions on an inner surface of the barrel 105 that are sufficient to prevent expulsion of the plunger 115. For example, as shown in FIG. 4C, in one arrangement, the interior surface of barrel 105 may further include an inwardly extending annular detent 210'.

The stopper 125 has an outer diameter that is slightly larger than the interior diameter of the barrel 105. While stopper 125 will compress when introduced into the barrel 105, the barrel flange 210 or annular detent 210' will prevent stopper 125 from being extracted from the barrel 105, as portion of the annular retainer 155 will come into contact with the barrel flange 210 and annular detent 210'.

In one exemplary method, an air bubble is intentionally left within the barrel after filling the chamber 230 with solution. The air bubble facilitates a large pressure differential and outward force of the plunger 110 during sterilization as an EtO sterilization cycle uses a deep draw vacuum. In another exemplary method, the chamber 230 is free of air bubbles. As described above, choice of silicone lubricant parameters may also affect plunger motion.

Disposed on the first end exterior of the barrel 105 is a gripping flange 235. The gripping flange 235 extends radially outwardly around the open first end 180 so as to be sized to be greater than a diameter of the barrel 105. In one exemplary arrangement, the gripping flange 235 extends all the way around the open first end 180. In another exemplary arrangement, the gripping flange 235 is configured with gaps between land areas. Both configurations allow a user to grip the barrel 105 while the plunger 130 is being moved inwardly within the chamber 230.

The barrel 105 may be manufactured with one or more plastic materials. However, in one exemplary arrangement, barrel 105 is formed of cyclic olefin polymer (COP) and/or cyclic olefin copolymer (COC) materials. These polymers are similar to glass in that they have high gas impermeability, high moisture barrier and low absorption rate properties. However, unlike glass, COC and COP materials are not fragile and do not have the weight and transport issues associated with glass. The barrel 105 may be coated with materials for increased barrier properties, such as silicone dioxide or aluminum dioxide. In another embodiment, the barrel 105 may be uncoated. Additionally or alternatively, the barrel 105 may be formed from materials having high clarity so that contents of the barrel may be visibly inspected. The barrel 105 may also be formed from materials having at least one of low water vapor permeability (in one example, less than about 0.5 g/m$^2$ per day per 330 micron thickness at atm to minimize moisture transmission across walls of the container), low oxygen permeability (in one example, less than about 500 cm$^3$/m$^2$ per day per 80 micron thickness at atm to minimize gas transmission across walls of the container), high heat resistance to withstand temperatures of autoclaving (in one example, the heat resistance is effective to standard autoclaving temperatures), and minimal leaching, elution, extraction, absorption or adsorption.

The barrel 105 may be configured to receive the plunger 110 at the barrel first end 180. The stopper 125 of the plunger 110 may be inserted at the first end 180. The stopper 125, along with the tip cap 115, may be configured to create the chamber 230 within the barrel 105. As explained above, the stopper 125 may have a relatively stiff elastic modulus and the wipers 150 may create a mating surface with the inside of the barrel 105. Thus, the stopper 125 may permit the plunger 110 to move along axis A within the barrel 105 and also create a seal within the barrel 105 to prevent any material from leaving the chamber 230. Moreover, the mating conical surfaces between the barrel 105 and the stopper 125 may also serve to prevent blood uptake after the prefilled syringe has been administered to a patient by preventing the plunger assembly 110 from recoiling upward after administration.

Referring to FIGS. 6A-7B, in one exemplary arrangement, the tip cap 115 may be configured as a female luer 220 configured to receive the mating male luer 200 extending from the barrel 105. The tip cap 115 may be configured to seal the syringe assembly 100 to assist in creating the chamber 230 within the barrel 105. In one exemplary arrangement, the tip cap 115 includes an insert 300 that is disposed in a housing member 302. The housing member 302 may be constructed of a substantially rigid material, such as polycarbonate or other suitable plastic, as the housing member 302 does not contact the material disposed within the chamber 230. The insert 300 includes a base member 304 and a neck 306. The base member 304 is disposed within a cavity 308 formed by inner flanges 310 that extend inwardly from an inner surface 312 of the housing member 302. In one exemplary arrangement, the inner flange 310 has an upwardly extending lip 314 that extends annularly around the insert 300 so as to lock the insert 300 into the housing member 302. The inner flanges 310 are separated from one another such that a void area 316 is created between adjacent flanges 310. While not shown, in one exemplary arrangement inner surface 312 may include threads.

The insert 300 is manipulated such that the base member 304 is disposed within the cavity 308 and retained within the housing member 302 by the inner flanges 310. With the insert 300 mechanically fixed to the housing member 302, the housing is disposed over the barrel neck 195, such that the insert 300 is inserted into the barrel neck 195 with the male luer 200 being received within a channel 318 of the insert with an interference fit. A locating member 320 is disposed within an opening formed within the male luer 200. The base member 304 fits against and seals a top surface of the barrel neck 195. In one exemplary arrangement, the inner surface 312 may include threads that cooperate with corresponding threads disposed on an exterior surface of the barrel neck 195 to lock the tip cap 115 onto the barrel 105.

As explained, the chamber 230 may be configured to hold the sterilization-sensitive material. Thus, a portion of the tip cap 115 may come in contact with the material during sterilization, shipping and storage of the syringe. In instances where a syringe assembly 100 is included in a package such as a surgical kit, a needle for insertion into the barrel neck 195 may also be included in the kit.

The tip cap 115 may be made of any number of materials. Exemplary materials may include polycarbonates that possess adequate barrier properties. For example, plastics such as polypropylene coated with a high-barrier material (e.g., butyl rubber) on at least a portion of the tip cap 115 may be used. The surface area of the tip cap 115 exposed to the material in the chamber 230 is relatively small compared to that of the barrel 105 and stopper 125. Thus, the portion exposed to the material may be coated, while the remaining portions of the tip cap 115 may not.

In another exemplary arrangement (not shown), the tip cap may be constructed entirely of butyl rubber and include a neck and a base member. The base member is configured with an outer diameter that is larger than an outer diameter of the neck area. Disposed within the neck area is a channel, similar to channel 318. The channel is also defined by an open end and a closed end. A locating element, similar to locating member 320 and may be fixedly disposed on the closed end of the channel.

In operation, the neck area is inserted into the barrel neck with the male luer being received within the channel with an interference fit. The locating member is disposed within an opening formed within the male luer 200. The base member fits against and seals a top surface of the barrel neck 195.

Figure 7A:
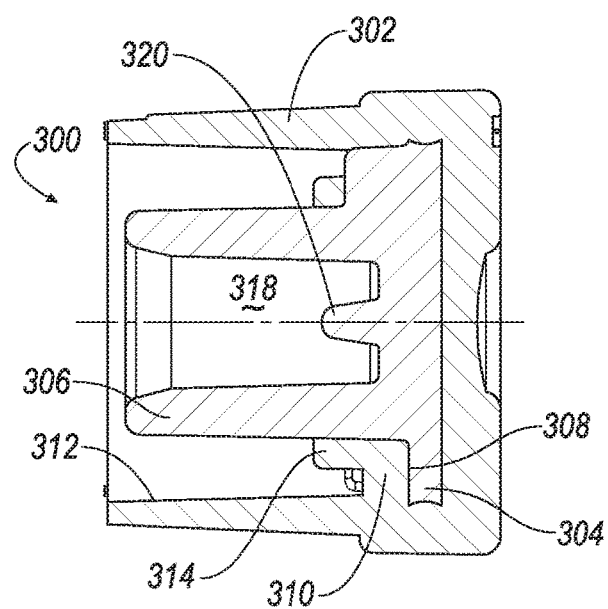
FIG. 7A is a cross-sectional view of the tip cap assembly of FIG. 6A.
Figure 7B:
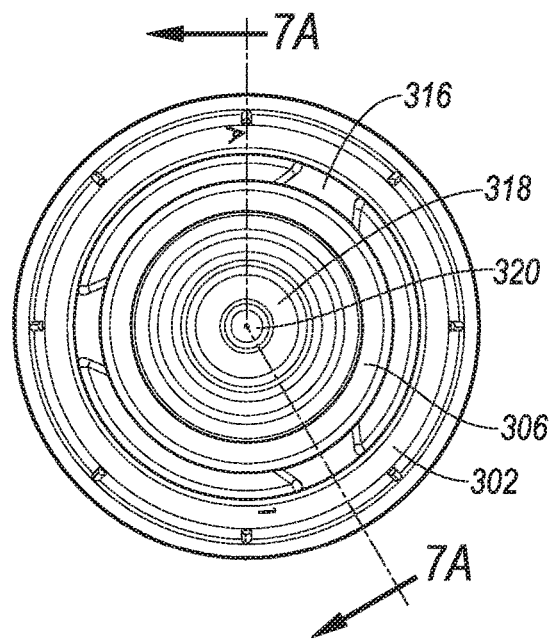
FIG. 7B is a plan view of the tip cap assembly of FIG. 7A.

Referring to FIGS. 7A and 7B is another exemplary arrangement; the tip cap 115 includes a butyl rubber insert 300 that is disposed in a housing member 302. The housing member 302 may be constructed of a substantially rigid material, such as polycarbonate or other suitable plastic, as the housing member 302 does not contact the material disposed within the chamber 230. The insert 300 includes a base member 304 and a neck 306. The base member 304 is disposed within a cavity 308 formed by inner flanges 310 that extend inwardly from an inner surface 312 of the housing member 302. In one exemplary arrangement, the inner flange 310 has an upwardly extending lip 314 that extends annularly around the insert 300 so as to lock the insert 300 into the housing member 302. The inner flanges 310 are separated from one another such that a void area 316 is created between adjacent flanges 310. While not shown, in one exemplary arrangement inner surface 312 may include threads.

Figure 5:
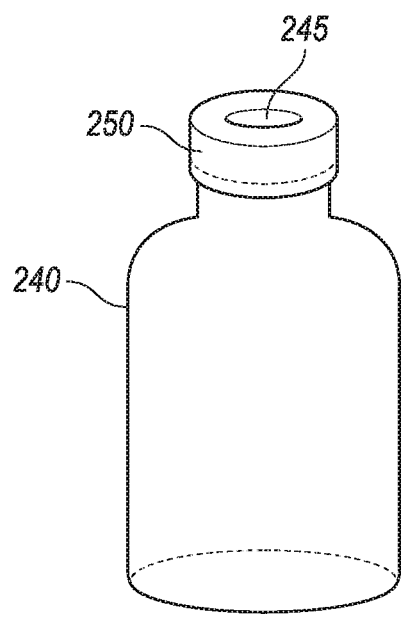
FIG. 5 illustrates a side view of an exemplary vial.

FIG. 5 shows an exemplary vial 240 including a stopper 245 and a cap 250. The vial 240 may be formed from COC or COP and the stopper 245 may include a region formed of a thermoplastic elastomer such as a butyl rubber. The stopper 245 may be fitted within a neck of the vial 240. The cap 250 may surround the top of the vial 240. The vial 240 may include sterilization sensitive material, similar to the syringe assembly 100 above. During sterilization, pressure may build within the vial and the cap 250 may be configured to abut at least a portion of the stopper 245 at the top of the vial to prevent the stopper 245 from being ejected from the vial 240 during pressure increases.

As explained above, the outside of the syringe assembly 100 and/or the vial 240 may be sterilized along with the other items within a surgical kit via a variety of sterilization techniques such as EtO sterilization and/or autoclaving. Prior to sterilization, the separate components of the syringe assembly 100 and the vial 240 (e.g., the barrel 105, plunger 110, tip cap 115, etc.) may be manufactured in a clean room environment. Additionally or alternatively, each component may be sterilized prior to assembly. Upon partial assembly of the components, the chamber 230 may be filled with the material. In one example, the stopper 125 of the plunger 110 may be inserted at the first end 180 of the barrel 105 and prior to attaching the tip cap 115 to the barrel neck 195, the material may be filled at the opening 205. The tip cap 115 may then be attached to the barrel 105 at the barrel neck 195, thus sealing the material within the chamber 230. In another example, the tip cap 115 may first be connected to the barrel neck 195 via the luer fitting and the material may be filled at the first end 180 prior to the plunger 110 being inserted into the barrel 105. Once the chamber 230 has been filled, and the plunger 110 inserted, the syringe assembly 100 may be sterilized.

For example, the assembly 100 may be placed in an autoclave. By subjecting the syringe assembly 100 to highly saturated steam, the exterior of the assembly may be sterilized. Further, the interior of the components, which will not be exposed to the steam, will also be sterilized due to high temperature of the container's solution therein. Once the syringe assembly 100 is removed from the autoclave, the outside of the assembly 100 may become non-sterile; however, the fluid and fluid path remain sterile. The syringe assembly 100 may be individually packaged (as single dose syringes or multiple syringes in a single package) or be combined with the remaining kit contents. The individual packages or the entire kit may then be sterilized via EtO sterilization. Thus, the outside of the assembly 100 is sterilized. For those arrangements that include packaging the syringe assembly 100 with the rest of the kit items, the outside of the assembly 100 may be sterilized simultaneously with the other kit components. Due to the specific properties of the barrel 105, plunger 110, stopper 125, and tip cap 115, the material within the chamber 230 is not altered or affected by the sterilization process.

In another alternative arrangement, once the syringe assembly 100 is removed from the autoclave, the syringe assemblies 100 (with or without sterilization sensitive material being disposed therein) may be placed in its own pouch with one or more vials 240 containing sterilization sensitive material. The packaged combination syringe assembly 100 and vial 240 may then be subjected to an EtO sterilization procedure. Finally, it is understood that the present disclosure also contemplates that vials, such as vial 240, that are constructed of COP or COC material with a suitable butyl rubber boundary, may be individually packaged (or included in a surgical kit) and subjected to an EtO sterilization process without adversely affecting sterilization sensitive material.

Advantageously, prefilled container systems may be packaged together with other materials requiring terminal sterilization as part of the manufacturing process and need not be separately packaged with materials having high barrier properties such as sealed, foil wrapping.

The inventors have found that by using COP or COC for the barrel of the syringe and employing a suitable sterilization protocol, no undesirable pH shift of the solution disposed within the chamber 230 after undergoing a suitable terminal sterilization procedure was experienced. More specifically, the inventors have developed a series of sterilization protocols that were tested on an exemplary arrangement of prototypes manufactured with a COP barrel and a tip cap manufactured from polypropylene with a chlorobutyl rubber insert.

One exemplary EtO sterilization cycle that the inventors have developed for successfully EtO sterilizing prefilled syringes has many processes, but generally can be classified into four basic groups of processes and/or parameters: 1) preprocessing or preconditioning; 2) chamber washes and conditioning; 3) sterilization and 4) evacuation. A first embodiment of the preprocessing group of processes/parameters for an exemplary EtO sterilization cycle is set forth in Table 1 below:

TABLE 1

| Category | Cycle Phase | Cycle Set Points | Tolerance Range |
| --- | --- | --- | --- |
| Preprocessing | Minimum Temp. prior to preconditioning | N/A | 40-125° F. |
| Preprocessing | Preconditioning Temp. | 100° F. | 90-130° F. |
| Preprocessing | Preconditioning Humidity | 60% | 45-95% |
| Preprocessing | Preconditioning Time (Hrs) | N/A | 6-96 |
| Preprocessing | Product % Relative humidity | N/A | 45-85% |
| Preprocessing | Product Temp. | N/A | 45-125° F. |

The preprocessing group of processes is designed to precondition the syringes to get any bacteria "active" or "excited" so as to make any bacteria/microorganisms grow and be more susceptible to EtO gas. To do this, the preprocessing group of processes seeks to raise the temperature and humidity to precondition the syringes and their contents. In one embodiment, the preprocessing group of processes starts by placing the syringes in a preconditioning area, such as, for example, a room or chamber, which is set at a minimum temperature. Alternatively, the preprocessing step may also be done in a sterilization chamber, which is used for other of the parameters of the sterilization cycles, as will be explained in further detail below. In one exemplary arrangement, the minimum initial starting temperature may be within the range of 40-125° F. In one particular example, the initial starting temperature may be room temperature, i.e., approximately 70° F.

From the initial starting temperature, the temperature in the preprocessing area is then raised to a preconditioning temperature. In one exemplary arrangement, the range of temperatures is within about 90-130° F. In another exemplary arrangement, the range of preconditioning temperatures may be within the range of 90-110° F. In one particular example, the preprocessing temperature is set to 100° F.

The humidity is also raised in the preprocessing group of processes. More specifically, the preconditioning humidity in the preprocessing area is raised to be in the range of 45-85% relative humidity. In another exemplary arrangement, the preconditioning humidity is raised in the range of 45-95%. In one particular example, the preconditioning humidity is set to be 60%.

To appropriately grow any bacteria/microorganisms, the syringes remain in the preprocessing area/chamber for a preprocessing time period. The time period is dependent upon the temperature of the product and the humidity of the product reaching the approximate temperature and humidity of the room/chamber. In one exemplary arrangement, the range of time for the syringes to remain in the preprocessing room/chamber is between 6 hours and 96 hours. In another exemplary arrangement, the range of time for the syringes to remain in the preprocessing room/chamber is between 18-96 hours. Before the syringes are subjected to sterilization processes, (and may be moved to the sterilization chamber, as explained in further detail below), the temperature of the syringes is in the range of 45-125° F. In another exemplary configuration, after preconditioning, the syringes are ± in the range of 90-110° F.

Additionally, after preconditioning, in one exemplary arrangement, the relative humidity of the syringes is within the range of 45-85%. In another exemplary arrangement, the relative humidity of the syringes is within the range of 45-95%.

Once the preprocessing group of processes/parameters is complete, if necessary, the syringes are then exposed or subjected to chamber washes and conditioning. A first embodiment of chamber washes and conditioning group of processes/parameters for an EtO sterilization cycle is set forth in Table 2 below:

TABLE 2

| Category | Cycle Phase | Cycle Set Points | Tolerance Range |
| --- | --- | --- | --- |
| Washing/Conditioning | Process Temperature | 115° F. | 85-130° F. |
| Washing/Conditioning | Initial Evacuation | 6 inHgA | 1.0-24.0 inHgA |
| Washing/Conditioning | Leak Test Chamber | 5 min. | 5-60 min. |
| Washing/Conditioning | Inject pressure change | N/A | .5-3.0 inHgA |
| Washing/Conditioning | Dwell pressure | N/A | 2.3-14 inHgA |
| Washing/Conditioning | Dwell time | N/A | 15-120 min |
| Washing/Conditioning | Relative humidity at end of dwell time | N/A | 47.6-91.9% |
| Washing/Conditioning | N2 Pressure | 28.0 inHgA | up to 30.5 inHgA |
| Washing/Conditioning | Second Evacuation | 6 inHgA | 1.0-24.0 inHgA |
| Washing/Conditioning | Repeat N2 evacuations | 2 | 0-4 |
| Washing/Conditioning | Inject pressure change | 1.5 inHgA | 0.5-3.0 inHgA |
| Washing/Conditioning | Dwell pressure | 6.5 inHgA | 2.3-14.0 inHgA |
| Washing/Conditioning | Dwell time | 75 min. | 15-120 min |

The washing/conditioning group of processes/parameters is performed to remove most (in one exemplary arrangement >97%) of the air from the chamber so the EO gas/air mixture is not explosive. In addition, the washing/conditioning group of processes/parameters is performed to add both moisture and heat to the area/chamber so when EO gas is injected into the chamber, the bacteria/microorganisms exposed in the preprocessing step above will be eradicated. Once the syringes are properly sealed in a suitable area, the temperature with the area/chamber is raised to a sterilization temperature. In one exemplary arrangement, the sterilization temperature is raised within the range of 85-130° F. In another exemplary arrangement, the sterilization temperature is raised within the range of 105-125° F. In yet another exemplary arrangement, a target temperature for the sterilization temperature is 115° F.

Simultaneous with raising the temperature to a sterilization temperature, the sterilization area is subjected to an evacuation process to remove air from the syringes. In one exemplary arrangement, the evacuation process applies vacuum pressure within a range of 1-24 inches of mercury absolute (inHgAl. In another exemplary arrangement, the initial evacuation process applies vacuum pressure of approximately 6 inHgA. In yet another exemplary arrangement, the initial evacuation process applies vacuum pressure of approximately 10 inHgA. An acceptable tolerance for vacuum pressure is 0.5 inHgA.

Once the evacuation process reaches a desirable set point, for example 10 inHgA, the vacuum may be turned off and a leak test is performed to verify that the that the sterilization area is properly sealed. If the evacuation pressure remains at the set point, within an acceptable tolerance for the duration of the leak test, then the washing/conditioning process proceeds to a pressure injection step. However, if the leak test fails, the sterilization area must be inspected for any failed seals and preprocessing procedure must be repeated for the syringes. In one exemplary arrangement, the leak test is performed within the range of 5-60 minutes. In one particular example, the leak test is performed for 5 minutes.

If the leak test is satisfactory, in one exemplary optional embodiment, moisture may be introduced into the syringes, such as by raising the relative humidity of the sterilization area until pressure within the sterilization area is raised to a predetermined pressure limit or the desired relative humidity set point is reached from direct measure (i.e., if the sterilization area includes one or more sensors to indicate the relative humidity). If the pressure injection step is omitted, the next step in the process is injecting Nitrogen gas into the sterilization area, discussed below.

For the humidity injection, in one example, the sterilization area (including the syringes) is injected with moisture to a target range of relative humidity of 0.5-3.0 inHgA to achieve a predetermined dwell pressure. In one exemplary arrangement, the dwell pressure may be within the range of 2.3-14.0 inHgA. Once the desired dwell pressure is reached, the relative humidity level is maintained for a predetermined dwell time. In one exemplary arrangement, the dwell time is within the range of 15-120 minutes. Once the dwell time has expired, the relative humidity of the sterilization area is confirmed. A relative humidity within the range of 47.6-91.9% has been determined by the inventors to be acceptable. If pressure injection fails, the cycle will be aborted.

After the humidity injection (or after the leak test if the humidity injection is omitted), next, Nitrogen gas is injected into the sterilization area under pressure. In one exemplary arrangement, Nitrogen gas is injected up to 30.5 inHgA. In another exemplary arrangement, Nitrogen gas is injected at approximately 28 inHgA. In another exemplary arrangement Nitrogen gas is injected with a range of 26-27 inHgA.

Next, the sterilization area undergoes another evacuation process. In one exemplary arrangement, the sterilization area is subjected to vacuum pressure within the range of 1-24 inHgA. In another exemplary arrangement, the sterilization chamber is subjected to a vacuum pressure set point of approximately 6 inHgA. In another exemplary arrangement, the sterilization area is subjected to a vacuum pressure set point of approximately 10 inHgA. The inventors have determined that a tolerance of 0.5 inHgA is acceptable for the second evacuation process.

After the Nitrogen evacuation process, the Nitrogen pressure/evacuation process outlined above may be repeated, though not required. For example, in one exemplary arrangement the Nitrogen pressure/evacuation process is repeated within the range of 1-4 times. In another exemplary arrangement, the Nitrogen pressure/evacuation process is repeated approximately 2 times. In another exemplary arrangement the Nitrogen pressure/evacuation process is repeated is repeated 3 times.

After the Nitrogen evacuation process, more water vapor may be introduced into the sterilization area to raise the relative humidity level. In one exemplary arrangement, the sterilization area (including the syringes) is injected with moisture to a target range of relative humidity of 0.5-3.0 inHgA. In another example, the sterilization area is injected with moisture to a target humidity of 1.5 inHgA, to achieve a predetermined dwell pressure. In one exemplary arrangement, the dwell pressure may be within the range of 2.3-14.0 inHgA. In another exemplary arrangement, a target dwell pressure may be within the range of 10-14 inHgA. In yet other exemplary arrangements, a target dwell pressure may be 6.5 or 11.5. Once the desired dwell pressure is reached, the relative humidity level is maintained for a predetermined dwell time. In one exemplary arrangement, the dwell time is within the range of 15-120 minutes. In another exemplary arrangement, a dwell time of 75.0 minutes has been found to be acceptable.

Once the chamber washes and conditioning group of processes is complete, the syringes are then subjected to an EtO sterilization process. A first embodiment of the EtO sterilization group of processes and parameters for an EtO sterilization cycle is set forth in Table 3 below:

TABLE 3

| Category | Cycle Phase | Cycle Set Points | Tolerance Range |
| --- | --- | --- | --- |
| EtO Sterilization | EtO injection | 20 inHgA | 10.7-29.9 inHgA |
| EtO Sterilization | EtO Concentration after EtO injection | 710 mg/L | 150-800 mg/L |
| EtO Sterilization | Nitrogen blanket | 27 inHgA | 25.5-30 inHgA |
| EtO Sterilization | Sterilization dwell time | 4 hours | 1-24 hours |
| EtO Sterilization | Sterilization dwell temperature | 102° F. | 102-140 |
| EtO Sterilization | EtO Supplement | 1 | 0-10 |

The EtO sterilization group of processes begins by introduction of EtO gas into the sterilization area until reaching a predetermined pressure level. In one exemplary arrangement, the pressure level is within the range of approximately 10.7-29.9 inHgA. In another exemplary arrangement, a target pressure level is 20 inHgA. In yet another exemplary arrangement, a target pressure level is 19 inHgA.

Next, the EtO concentration within the sterilization area is verified to be with a preset target level after EtO injection. In one exemplary arrangement, a suitable target range is 150-800 mg/L. In another exemplary arrangement, a target range of approximately 315-474.5 mg/L In one exemplary arrangement, a set target of 421.7 mg/L is desirable. Alternatively, a biologic indicator may be used to verify the EtO concentration within the sterilization chamber.

Once the EtO concentration has been reached, a nitrogen blanket may be introduced. In one exemplary arrangement the nitrogen blanket target range is up to 30 inHgA. In another exemplar arrangement, a suitable target range may be between 25.5-27.0 inHgA.

The EtO concentration within the sterilization area is maintained at a set temperature for a suitable dwell time. In one exemplary arrangement, the dwell temperature is within the range 102-140° F. Alternatively, the dwell temperature may be within the range of 110-125° F. The dwell time may be within the range of 1-24 hours. In another example, the dwell time may be within the range of 4-8 hours. In yet another exemplary arrangement, a dwell time of 4 hours is utilized.

During the dwell time, if the EtO concentration falls below a predetermined set point, additional EtO supplements may be injected until the EtO concentration can be maintained above the set point for a minimum dwell time. EtO injections may be employed up to 10 times during an EtO sterilization procedure.

Once the EtO sterilization group of processes is complete, the syringes are then subjected to a wash and post exposure process. A first embodiment of the wash and post exposure group of processes/parameters for an EtO sterilization cycle is set forth in Table 4 below.

TABLE 4

| Category | Cycle Phase | Cycle Set Points | Tolerance Range |
| --- | --- | --- | --- |
| Wash/Exposure | Evacuation | 6 inHgA | 1-24 inHgA |
| Wash/Exposure | Nitrogen injection | 27 inHgA | up to 30.5 inHgA |
| Wash/Exposure | Repeat Nitrogen washes | 3 | 0-4 |
| Wash/Exposure | Evacuation | 6 inHgA | 1-24 inHgA |
| Wash/Exposure | Air Injection | 27.0 | up to 30.5 inHgA |
| Wash/Exposure | Repeat air washes | 3 | 0-8 |
| Wash/Exposure | Airbreak to atmosphere | 28.00 Hg | 27.5-ATM |

The wash/exposure group of processes/parameters begins by evacuating EtO gas and Nitrogen from the sterilization area to remove EtO gas from the sterilization area. In one exemplary arrangement a vacuum pressure is applied to the sterilization area within the range of 1-24 inHgA. A vacuum pressure of 6 inHgA has been found to be a suitable vacuum level by the inventors of the present application. The evacuation pressure is applied between 1 and 30 minutes.

Next, Nitrogen gas is injected into the sterilization chamber under pressure. In one exemplary arrangement, Nitrogen gas is injected up to 30.5 inHgA. In another exemplary arrangement, Nitrogen gas is injected at approximately 27 inHgA. In another exemplary arrangement Nitrogen gas is injected with a range of 27-28 inHgA. The nitrogen gas injection is performed for 1 to 30 minutes. This process may be repeated up to 4 times. In one exemplary arrangement, the Nitrogen gas injection is repeated three times.

After completing the Nitrogen gas injections, the sterilization area is evacuated to an evacuation pressure. In one exemplary arrangement, a vacuum pressure of approximately 1-24 inHgA is applied. In another exemplary arrangement, a vacuum pressure of 6 inHgA has been found to be acceptable. In yet another example, a vacuum pressure of 10 inHgA has been found to be acceptable.

Next, the sterilization area undergoes an air wash step. Air is injected under pressure between up to 30.5 inHgA. In one exemplary arrangement, the pressure range for the air wash is between 27-28 inHgA. The sterilization area is subjected to the air wash for 1 to 30 minutes. The air washes may be repeated up to 6 times. In one exemplary arrangement, the air wash may be repeated 3 times. In another exemplary arrangement, the air wash process may be repeated 4 times.

After the air washes are completed, the sterilization area is opened to the atmosphere and product pallets containing the prefilled syringes may be removed and taken to an aeration facility within the manufacturing facility, as well be explained in further detail below. Alternatively, the product pallets may remain the sterilization area. In one exemplary arrangement, the aeration temperature within the aeration area of the facility may be within the range of 95-120° F. The product pallets may be aerated within the range of 24-120 hours.

Figure 8:
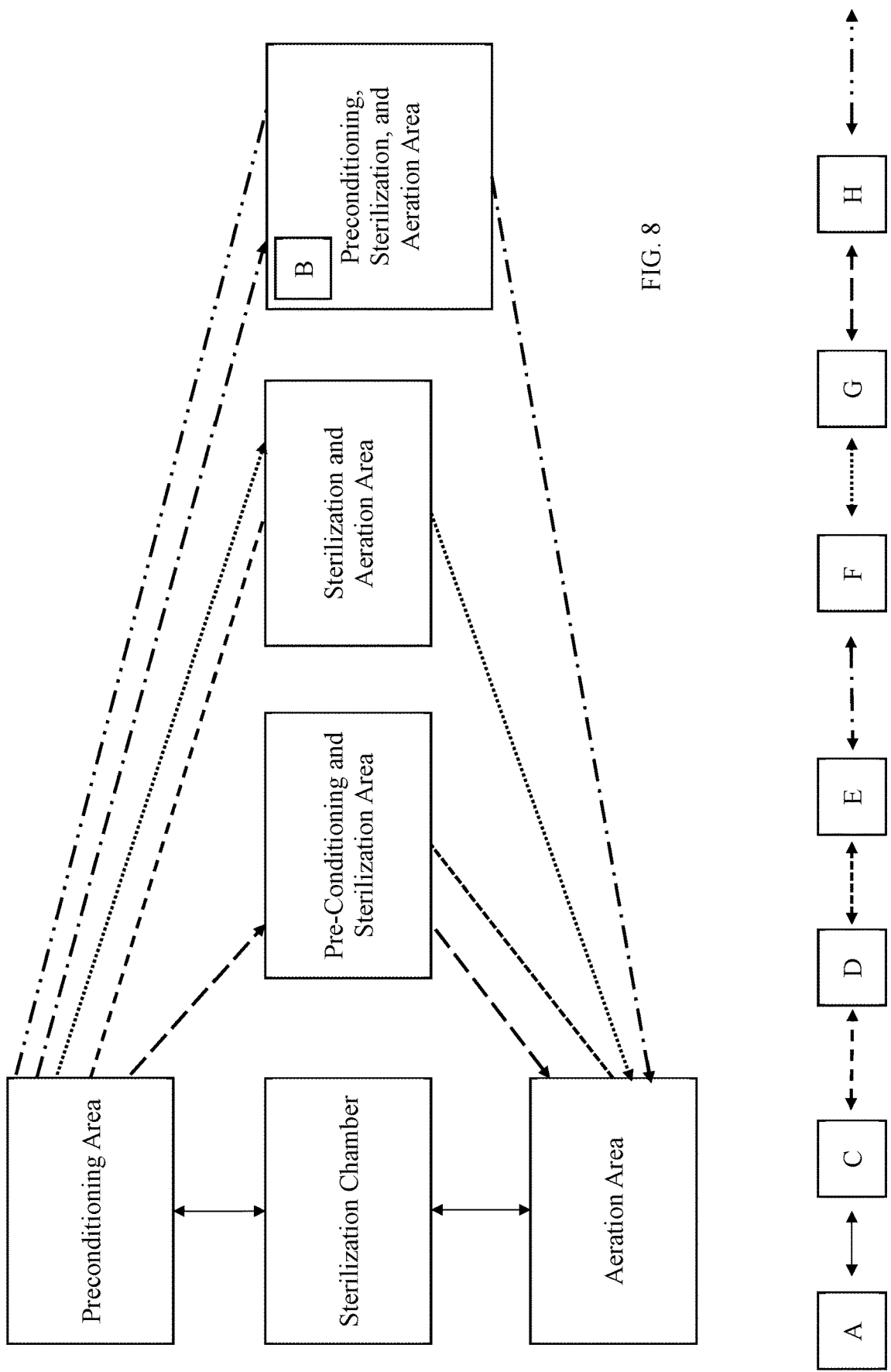
FIG. 8 is a flow chart illustrating various product flow paths for groups of EtO sterilization processes.

Referring to FIG. 8, configurations of the sterilization protocols will now be discussed. More specifically, the flow chart in FIG. 8 represents alternative product flow (i.e., syringes, vials or other items) for sterilization protocols discussed herein. For ease of explanation, the product flow will be described in the context of EtO sterilization of a syringe.

In a first arrangement, represented by solid arrow lines A, the preprocessing/preconditioning group of processes begins with the syringe (or group of syringes) being placed in a preconditioning area within a facility. The preprocessing/preconditioning group of processes are then all performed in the preconditioning area. Once the preprocessing/preconditioning group of processes are completed, the syringes are then moved to a sterilization chamber/area. Once in the sterilization chamber/area, in product flow A, the syringes are subjected to the chamber washes/conditioning, sterilization and evacuation group of processes. Finally, the syringes may then be moved to an aeration area to aerate the syringes.

In another alternative arrangement, all of the group of processes (i.e., preprocessing/preconditioning, chamber washes/conditioning, sterilization and evacuation, (including aeration) may be done as an "all-in-one" process in a single area or chamber. This product flow is represented by element B in FIG. 8.

As a further alternative arrangement, represented by dashed line C, the product flow comprises the preprocess/preconditioning group of processes being performed in a preprocessing area/chamber. Once completed, the syringes are moved to a sterilization chamber/area, where the remaining groups of processes are conducted (i e, the chamber washes/conditioning, sterilization and evacuation, including aeration).

In the product flow arrangement represented by small dashed line D, the syringes undergo the preprocessing/preconditioning group of processes and the chamber washes/conditioning and sterilization group of processes in the same location, such as in a sterilization chamber/area. Once evacuation of the chamber/area is completed, the syringes are then moved to an aeration area in a facility.

Product flow arrangements represented by product flow paths E-H, involves repeating certain aspects of the groups of processes. More specifically, product flow path represented by a dot alternating with a dash line E involves, first subjecting the syringes to the preprocessing group of steps in the preconditioning area. Next, the syringes are moved to sterilization chamber where the preconditioning group of processes are repeated and the chamber washes/conditioning, sterilization and evacuation (including aeration) group of processes are completed. The syringes are then moved to the aeration area in the facility and may be aerated again.

In the product flow arrangement represented by the small dotted line F, the syringes are first subjected to the preprocessing group of steps in a preconditioning area. Next, the syringes are moved to a sterilization chamber where chamber washes/conditioning, sterilization and evacuation groups of processes are conducted. The syringes are then moved to the aeration area in the facility and may be aerated again.

The product flow arrangement represented by long dashed lines G involves first subjecting the syringes to the preprocessing group of steps in a preconditioning area. Next, the syringes are moved to a sterilization chamber/araa, where the preprocessing group of steps of repeated, and where the chamber washes/conditioning, sterilization and evacuation groups of processes are conducted. The syringes are then moved to the aeration facility and may be aerated.

An additional alternative product flow arrangement is represented by double dot dashed line H. In this arrangement, the syringes are subjected to the preprocessing group of steps in a preconditioning area. Next, the syringes are moved to a sterilization chamber whereby the syringes then undergo another preprocessing/preconditioning step, as well as subjecting the syringes to the chamber washes/conditioning, sterilization and evacuation group of steps, including aeration.

A series of test samples were prepared for verifying the effectiveness of the sterilization procedures described above. The sample size for testing included 60 total prefilled syringe assemblies 100, divided into six groups of 10 syringe assemblies 100. Each chamber 230 of the respective syringe assemblies 100 includes a chamber 230 of the barrel 105 filed with 5 mL of saline and the tip cap 115 is secured at the end of the barrel 105. One set of 10 syringe assemblies 100 was selected as being the Control Samples (identified as Group 1) and set aside, without performing any sterilization procedure.

A second set of 10 syringe assemblies 100 was designated as Group 2. The Group 2 syringes were exposed to two EtO sterilization cycles (as discussed in further detail below).

A third set of 10 syringe assemblies 100 was designated as Group 3. The Group 3 syringe assemblies 100 were exposed to steam sterilization only.

A fourth set of 10 syringe assemblies 100 was designated as Group 4. The Group 4 syringe assemblies 100 were exposed to steam sterilization and two EtO sterilization cycles (set forth below).

A fifth set of 10 syringe assemblies 100 was designated as Group 5. The Group 5 syringe assemblies 100 were exposed to one EtO sterilization cycle (set forth below).

A final set of 10 syringe assemblies 100 was designated as Group 6. The Group 6 was exposed to steam sterilization and one EtO sterilization cycle (set forth below).

The NaCl saline solution from each syringe in Groups 1-6 were tested for pH using an acceptable testing protocol for determining pH readings with an accuracy level of ±0.02 pH. The NaCl saline solution from each syringe in the Control Group (Group 1) and Groups 2, 4, and 6 were tested for EO and ECH residuals using an acceptable testing protocol, such as one using gas chromatography with a flame ionization detector. The average results of the testing for each group are set forth in Table 5 table below:

TABLE 5

| Sample # | Residual EO | Residual ECH | Avg. pH | Avg. pH shift (from control) |
|---|---|---|---|---|
| Control Samples Group 1 | <0.8 ppm | <0.6 ppm | 5.53 | |
| Group 2 | <0.8 ppm | <0.6 ppm | 5.59 | 0.054 |
| Group 3 | Not tested | Not tested | 4.85 | −0.683 |
| Group 4 | <0.8 ppm | <1.4 ppm | 4.86 | −0.691 |
| Group 5 | <0.8 ppm | <0.6 ppm | 5.38 | −0.153 |
| Group 6 | <5.4 ppm | <0.6 ppm | 5.17 | −0.363 |

As can be seen from the table above, the pH shift is within acceptable ranges resulting pH levels well within the USP requirements. More specifically, the pH for the solution in Groups 2-6 all fall within the range of 4.5-7.0. Moreover, the residual EO and ECH are also well within the FDA requirements. More specifically, the EO residual results are below the limit of 4 mg/device and the ECH residual results are below the limit of 9 mg/device.

The present disclosure provides a manufacturing methods, EtO sterilization processes and cycles, parameters, and ranges, for regulatory compliant production and EtO gas sterilization (post filling and autoclaving) of polymer prefilled containers, such as syringes, as well as vials. Suitable materials for such prefilled containers include 0.9% NaCl normal saline, heparinized saline, or other liquids. Correct application of the above complex methods create resultant sterile prefilled container without EtO gas ingress to EtO sensitive fluid within the container. The methods disclosed herein do not create the many possible unacceptable side effects of EtO gas ingress, such as pH shift outside the range of 4.5 to 7.0; toxic byproducts like EO-EC-EG residuals; 0.9% NaCl potency shift more than ±5%, alteration of contents (mL) due to plunger motion and leakage caused by an inappropriate selection of the nominal value of one or more of 30+ EtO sterilization process cycle parameters. The discovery of these disclosed methods has resulted in the ability to include non-glass pre-filled containers, such as syringes and vials, that can safely be put unpackaged (i.e., without additional user, inconvenient protective ETO barrier over-packaging-foil, etc.) into a standard breathable medical procedure sterile tray (i.e., convenience tray), kit pouch, or package with other components, or individually package the containers and be subjected to EtO sterilization and directly ready for infusion when it is extracted from its packaging or lifted out of the sterile procedure tray by the operating technician.

With regard to the processes, systems, methods, heuristics, etc. described herein, it should be understood that, although the steps of such processes, etc. have been described as occurring according to a certain ordered sequence, such processes could be practiced with the described steps performed in an order other than the order described herein. It further should be understood that certain steps could be performed simultaneously, that other steps could be added, or that certain steps described herein could be omitted. In other words, the descriptions of processes herein are provided for the purpose of illustrating certain embodiments, and should in no way be construed so as to limit the claimed invention.

Accordingly, it is to be understood that the above description is intended to be illustrative and not restrictive. Many embodiments and applications other than the examples provided would be apparent upon reading the above description. The scope of the invention should be determined, not with reference to the above description, but should instead be determined with reference to the appended claims, along with the full scope of equivalents to which such claims are entitled. It is anticipated and intended that future developments will occur in the arts discussed herein, and that the disclosed systems and methods will be incorporated into such future embodiments. In sum, it should be understood that the invention is capable of modification and variation and is limited only by the following claims.

All terms used in the claims are intended to be given their broadest reasonable constructions and their ordinary meanings as understood by those skilled in the art unless an explicit indication to the contrary in made herein. In particular, use of the singular articles such as "a," "the," "said." etc. should be read to recite one or more of the indicated elements unless a claim recites an explicit limitation to the contrary.

The invention claimed is:

1. A method of EtO sterilizing a prefilled syringe, comprising:
   providing a syringe prefilled with a sterilization-sensitive material, the sterilization-sensitive material being adversely affected when exposed to ethylene oxide (EtO) and having an initial pH within an acceptable pH range as defined by the United States Pharmacopeia;
   initiating a preprocessing stage of an EtO sterilization procedure cycle on the syringe to initiate growth of microorganisms on an exterior of the syringe] initiating a wash and conditioning stage of the EtO sterilization procedure cycle on the syringe to remove air from both the syringe and a treatment chamber containing the syringe, wherein the wash and conditioning stage includes raising a temperature of the treatment chamber to a conditioning temperature within a range of 85-130° F.;
   initiating an EtO sterilization stage of the EtO sterilization procedure cycle on the syringe within the treatment chamber to sterilize the exterior of the syringe; and
   initiating a wash and post exposure process of the EtO sterilization procedure cycle to remove EtO gas from the treatment chamber;
   wherein upon completing the EtO sterilization procedure cycle, a resultant pH of the sterilization-sensitive material remains within the acceptable pH range as defined by the United States Pharmacopeia.

2. The method of claim 1, wherein a barrel of the syringe is formed of at least one of a cyclic olefin polymer (COP) and a cyclic olefin copolymer (COC).

3. The method of claim 1, wherein the sterilization-sensitive material includes at least one of saline, heparinized saline and lidocaine, and wherein the acceptable pH range is between 4.5-7.0.

4. The method of claim 1, wherein the sterilization-sensitive material includes at least one of lidocaine hydrochloride and heparin, and wherein the acceptable pH range is between 5.0-7.0.

5. The method of claim 1, wherein the sterilization-sensitive material includes lidocaine hydrochloride and epinephrine.

6. The method of claim 1, wherein the preprocessing stage further comprises raising the temperature and humidity of a preconditioning area into which the syringe is located to a predetermined level to initiate the growth of the microorganisms.

7. The method of claim 6, wherein the temperature of the preconditioning area is within a first range of 90-130° F., wherein the humidity of the preconditioning area is within a second range of 45-95%, and wherein a dwell time for maintaining the predetermined level of the temperature and humidity of the preconditioning area is within a third range of 6-96 hours.

8. The method of claim 6 wherein the preconditioning area is also the treatment chamber.

9. The method of claim 1, wherein the wash and conditioning stage includes moving the syringe to the treatment chamber and sealing the treatment chamber.

10. The method of claim 1, further comprising:
initiating an evacuation process simultaneous with raising the temperature to the conditioning temperature; and
performing a leak test for a predetermined time period within a range of 5-60 minutes.

11. The method of claim 10, wherein the evacuation process applies vacuum pressure within a range of 1-24 inches of mercury absolute (inHgA).

12. The method of claim 10, wherein the evacuation process applies vacuum pressure to a set point of 10 inches of mercury absolute (inHgA), within a tolerance of ±0.5 inHgA.

13. The method of claim 10, further comprising introducing moisture into the treatment chamber to a target range of 0.5-3.0 inches of mercury absolute (inHgA) relative humidity to achieve a predetermined dwell pressure.

14. The method of claim 13, wherein the predetermined dwell pressure is within a range of 2.3-14 inHgA, and wherein the dwell pressure is maintained for a dwell time within a range of 15-120 minutes.

15. The method of claim 13, further comprising injecting Nitrogen gas under pressure into the treatment chamber.

16. The method of claim 15, wherein the Nitrogen gas is injected up to 30.5 inHgA.

17. The method of claim 16, further comprising evacuating the treatment chamber by subjecting the treatment chamber to a pressure set point within a range of 1-24 inHgA.

18. The method of claim 17, further comprising introducing moisture into the treatment chamber to a target range of 0.5-30 inHgA to achieve a predetermined dwell pressure.

19. The method of claim 18, further comprising maintaining the dwell pressure for a dwell time within a range of 15-120 minutes, and wherein the predetermined dwell pressure is within a range of 2.3-14.0 inHgA.

20. The method of claim 1, wherein the wash and post exposure stage further comprises evacuating the EtO gas introduced during the EtO sterilization stage by application of vacuum pressure.

21. The method of claim 20, wherein the vacuum pressure is applied within a first range of 1-24 inches of mercury absolute (inHgA) for a time period in a second range of 1 to 30 minutes.

22. The method of claim 21, further comprising injecting additional Nitrogen gas into the treatment chamber containing the syringe under pressure up to 30.5 inHgA.

23. The method of claim 1, further comprising placing the syringe into an EtO serializable packaging with other surgical equipment, sealing the EtO serializable packaging with the assembled syringe and the other surgical equipment therein, before performing the EtO sterilization procedure cycle.

24. The method of claim 1, wherein upon completing the EtO sterilization procedure cycle, residual ethylene oxide and ethylene chlorohydrin levels in the sterilization-sensitive material does not exceed 10 ppm.

25. The method of claim 1, wherein residual ethylene glycol level in the sterilization-sensitive material does not exceed 20 ppm.

26. A method of EtO sterilizing a prefilled syringe, comprising:
providing a syringe prefilled with a sterilization-sensitive material, the sterilization-sensitive material being adversely affected when exposed to ethylene oxide (EtO) and having an initial pH within an acceptable pH range as defined by the United States Pharmacopeia;
initiating a preprocessing stage of an EtO sterilization procedure cycle on the syringe to initiate growth of microorganisms on an exterior of the syringe;
initiating a wash and conditioning stage of the EtO sterilization procedure cycle on the syringe to remove air from both the syringe and a treatment chamber containing the syringe;
initiating an EtO sterilization stage of the EtO sterilization procedure cycle on the syringe within the treatment chamber to sterilize the exterior of the syringe; and
initiating a wash and post exposure process of the EtO sterilization procedure cycle to remove EtO gas from the treatment chamber;
evacuating the treatment chamber to a pressure within a range of 1-24 inches of mercury absolute (inHgA);
wherein upon completing the EtO sterilization procedure cycle, a resultant pH of the sterilization-sensitive material remains within the acceptable pH range as defined by the United States Pharmacopeia.

27. The method of claim 26, further comprising injecting air under pressure up to 30.5 inHgA to initiate an air wash of the treatment chamber.

28. A method of sterilizing a surgical kit containing a prefilled syringe, comprising:
providing a surgical kit, the surgical kit including a procedure tray having secured therein a syringe that has a non-glass barrel prefilled with a sterilization-sensitive material, wherein the sterilization-sensitive material is a material that is adversely affected when exposed to ethylene oxide (EtO) and has an initial pH within an acceptable pH range as defined by the United States Pharmacopeia;
initiating a preprocessing stage of an EtO sterilization procedure cycle on the surgical kit to initiate growth of microorganisms on an exterior of the syringe;
initiating a wash and conditioning stage of the EtO sterilization procedure cycle on the surgical kit to remove air from both the syringe and a treatment chamber containing the surgical kit;
initiating an EtO sterilization stage of the EtO sterilization procedure cycle on the surgical kit within the treatment chamber to sterilize the exterior of the syringe, wherein the wash and conditioning stage includes raising a temperature of the treatment chamber to a conditioning temperature within a range of 85-130° F.;
and initiating a wash and post exposure stage of the EtO sterilization procedure cycle to remove EtO gas from the treatment chamber;
wherein upon completing the EtO sterilization procedure cycle, a resultant pH of the sterilization-sensitive material remains within an acceptable pH range as defined by the United States Pharmacopeia.

* * * * *